United States Patent [19]

Bemis et al.

[11] Patent Number: 4,948,565

[45] Date of Patent: Aug. 14, 1990

[54] ANALYTICAL SYSTEM

[75] Inventors: William G. Bemis, Westford; John S. Uccello, Burlington, both of Mass.

[73] Assignee: Fisher Scientific Company, Pittsburgh, Pa.

[21] Appl. No.: 343,014

[22] Filed: Apr. 25, 1989

[51] Int. Cl.$^5$ .............................................. G01N 1/20
[52] U.S. Cl. ................................. 422/103; 73/863.73; 73/864.12; 251/355
[58] Field of Search ............... 422/103, 100; 436/180; 73/863.73, 864.12; 251/355

[56]  References Cited

U.S. PATENT DOCUMENTS

| | | | |
|---|---|---|---|
| 3,567,389 | 3/1971 | Coulter | 23/253 |
| 3,621,719 | 11/1971 | Goodman | 73/422 GC |
| 3,975,946 | 8/1976 | Ball | 73/61.1 C |
| 3,990,853 | 11/1976 | Godin | 23/259 |
| 3,991,055 | 11/1976 | Godin | 23/259 |
| 4,152,391 | 5/1979 | Cabrera | 422/103 |
| 4,299,794 | 11/1981 | Kelley | 422/50 |
| 4,444,066 | 4/1984 | Ogle | 73/863.72 |
| 4,445,391 | 5/1984 | Cabrera | 73/864.12 |
| 4,507,977 | 4/1985 | Cabrera | 422/103 X |
| 4,520,108 | 5/1985 | Yoshida | 436/52 |
| 4,702,889 | 10/1987 | Cabrera et al. | 251/355 X |
| 4,710,355 | 12/1987 | Ushikubo | 422/103 X |
| 4,726,932 | 2/1988 | Feier et al. | 73/863.73 X |
| 4,729,876 | 3/1988 | Hennessy | 422/103 |
| 4,822,569 | 4/1989 | Pellegrino | 73/864.12 X |

Primary Examiner—Robert J. Warden
Assistant Examiner—Lynn M. Kummert
Attorney, Agent, or Firm—Fish & Richardson

[57] ABSTRACT

A metering valve assembly for use in an analytical system includes fixed and movable valve members that have slidably engaged faces. One valve member includes a first metering chamber in the form of a through passage having an axis perpendicular to the direction of relative valve motion and a second metering chamber of elongated shape that has a length at least three times its width and that extends along the direction of relative valve motion. In a first position, the metering chambers are connected in series with a source of the sample liquid to be analyzed; and in a second valve assembly position, the first metering chamber is connected in series between a source of auxiliary fluid and a first analysis unit and the second metering chamber is concurrently connected in series between a source of auxiliary fluid and a second analysis unit.

23 Claims, 3 Drawing Sheets

ANALYTICAL SYSTEM

This invention relates to analytical systems and more particularly to metering valve arrangements for use in analytical systems.

Metering valve arrangements are used in a number of different analytical systems including chromatography systems and hematology systems. A particular hematology system employs a metering valve system for measuring and dispensing precise microliter volumes of a sample to be analyzed, the valve having a first metering chamber in a rotor member and a second (larger) metering chamber attached to and external of a stator member, the system connecting the two measuring chambers in series relation in a first valve position, and flowing measured liquid volumes from the two metering chambers, each with a respective known volume of diluent, to different predetermined locations in a second valve position. A rotary metering valve of this type is disclosed in U.S. Pat. No. 4,822,569, for example.

In accordance with one aspect of the invention, there is provided a metering valve assembly for use in an analytical system that includes fixed and movable valve members that have slidably engaged faces. One valve member includes a first metering chamber in the form of a through passage having an axis perpendicular to the direction of relative valve motion and a second metering chamber of elongated shape that has a length at least three times its width and that extends along the direction of relative valve motion. In a first position, the metering chambers are connected in series with a source of the sample liquid to be analyzed; and in a second valve assembly position, the first metering chamber is connected in series between a source of auxiliary fluid and a first analysis unit and the second metering chamber is concurrently connected in series between a source of auxiliary fluid and a second analysis unit. Thus, two different quantities of sample to be analyzed may be serially loaded into two metering chambers and then concurrently dispensed from those metering chambers to two different analysis units.

Preferably, the two metering chambers are disposed in a movable valve member; the movable valve member is interposed between two fixed (stator) valve members with the opposite faces of the movable valve member in slidable engagement with surfaces of the two stator members; and the volume of the second metering chamber is at least ten times the volume of the first metering chamber.

In a particular embodiment, the movable valve member is a rotor member mounted for rotation between two stator members; its elongated metering chamber is of arcuate configuration; the volume of the through metering chamber is less than two microliters; and the volume of the arcuate metering chamber is greater than twenty microliters. The elongated arcuate metering chamber includes aligned inlet and outlet regions in opposite faces of the rotor member and a divider member that extends from the inlet and outlet regions along the length of the arcuate chamber to a through passage at the end of the arcuate chamber remote from the inlet and outlet regions such that two aligned grooves of arcuate configuration are formed in opposed surfaces of the rotor. While the series interconnection between the two metering chambers in the first valve position may be variously formed, including an integral interconnection in one of the stator members for example, in a particular embodiment, that interconnection is provided by a coupling loop connected to and external of a stator member.

In accordance with another aspect of the invention, there is provided a metering valve assembly for use in an analytical system that includes first and second valve members that have faces in slidable, sealing engagement with one another, and structure defining first and second metering chambers. The valve members have a first valve position in which the metering chambers are connected in series for serial receipt of sample liquid to be analyzed, and a second valve position in which the first metering chamber is adapted to be connected in series between a source of auxiliary fluid and a first analysis unit and the second metering chamber is adapted to be concurrently connected in series between a source of auxiliary fluid and a second analysis unit. Drive structure produces relative movement of the first and second valve members between the first and second valve positions, sensor structure is disposed adjacent the drive structure, and position indicator structure is coupled to the drive structure adjacent the sensor structure. The indicator structure includes a series of indicia that cooperate with the sensor structure to provide a first indication when the valve members are in the first valve position and a second indication when said valve members are in the second valve position.

In preferred embodiments, the drive structure includes a drive shaft and a stepper motor for driving a valve rotor member, the position indicator structure includes an encoder disc mounted on the drive shaft, the indicia are a series of openings in the encoder disc, and the sensor structure is of the optical sensor type.

In a particular embodiment, each of the valve members includes a plurality of flow passages, the sensor structure includes a first sensor for sensing indicia on said position indicator structure and corroboration sensor structure for supplementing the first sensor, and the assembly includes means for varying the angular position of the first sensor relative to the valve members to provide effective coordination of the position of the first sensor with flow passages in one of the valve members. The valve includes two stator members between which a rotor member is disposed and driven by a stepper motor. Also mounted on a shaft is a position indicator disc which has an array of radially extending edge surfaces that cooperate with first and corroboration sensors to provide rotor position indications. The shaft extends through the rotor and stator members; one stator member is seated against a reference member and a detachable external shaft extension carries a compression spring that biases the other stator member so that the valve components are urged into sealing engagement with one another. The arrangement provides a reliable valving arrangement that is easy to disassemble and to reassemble for cleaning or maintenance, as well as providing accurate reproducible positioning of the rotor relative to the stator members during metering operations of the valve.

Other features and advantages of the invention will be seen as the following description of a particular embodiment progresses, in conjunction with the drawings, in which.

DESCRIPTION OF PARTICULAR EMBODIMENT

Figure 1:
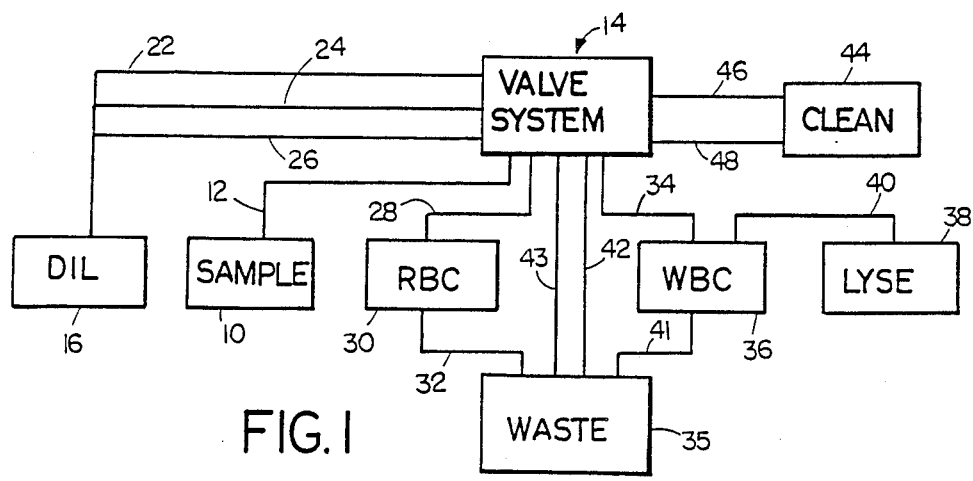
FIG. 1 is a block diagram of an analytical system in accordance with the invention.

FIG. 1 is a diagrammatic view of a hematology system for quantitative determination of white blood cell (WBC) counts and red blood cell (RBC) counts of a blood sample. The system includes sample source 10 which is connected to supply a sample of blood to be analyzed over line 12 to metering valve assembly 14. Diluent is supplied from source 16 to valve assembly 14 over lines 22, 24 and 26. A metered quantity of blood sample with diluent is transferred over line 28 to RBC analyzer unit 30, and after analysis, the diluted sample is discarded over line 32 to waste container 35. Similarly, a diluted metered quantity of blood sample is transferred over line 34 to WBC analyzer unit 36, and lyse material for processing the white blood count is obtained from container 38 and transferred into WBC analyzer unit 36. Lyse may be transferred directly from container 38 to WBC analyzer unit over line 40 as shown in FIG. 1; or diluent can push a measured amount of lyse through valve assembly 14 ahead of or, preferably, behind an aliquot of sample of defined volume After analysis, the sample is discarded over line 41 to waste container 35. A source of cleaning fluid 44 is connected by lines 46 and 48 to the valve assembly 14 and valve assembly 14 is connected to waste container 35 over lines 42 and 43.

Figure 3:
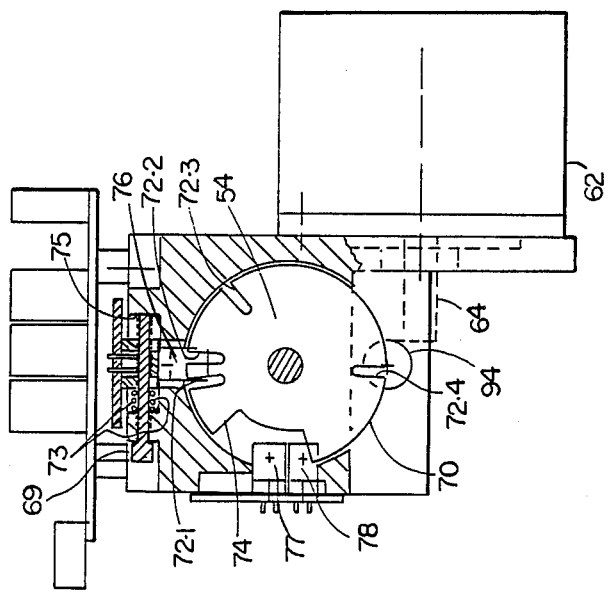
FIG. 3 is a sectional view taken along the line 3—3 of FIG. 2.
Figure 2:
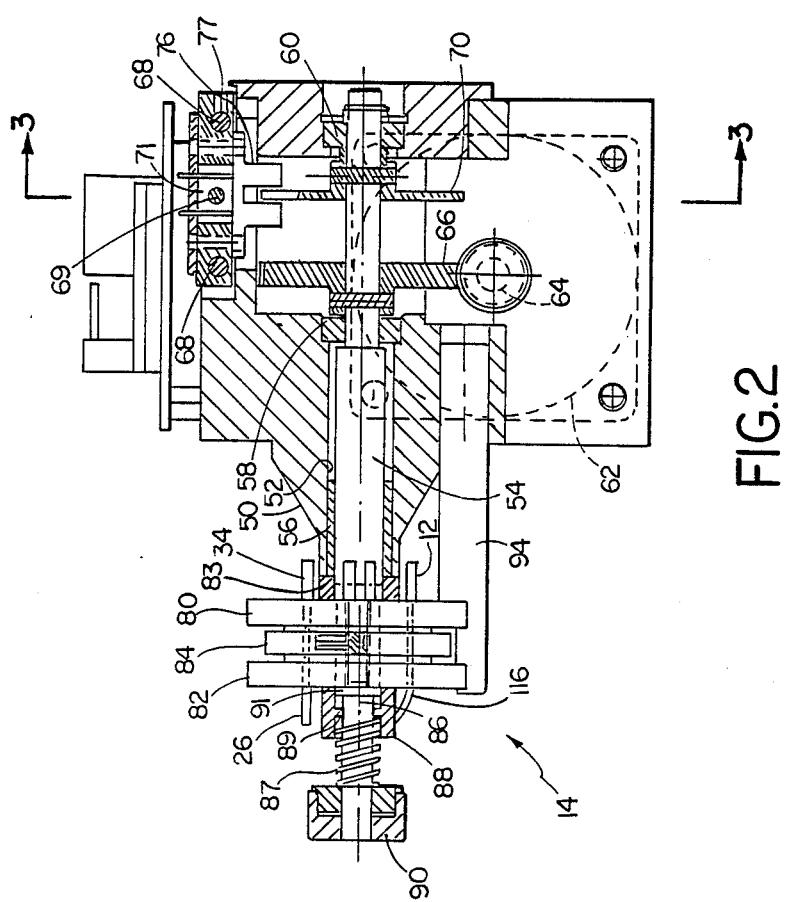
FIG. 2 is a view, partially in section, of the metering valve assembly employed in the system shown in FIG. 1.

Further details of the metering valve assembly 14 may be seen with reference to FIGS. 2–5. Valve assembly 14 includes housing member 50 with bore 52 in which a drive shaft 54 is supported for rotation by sleeve bearing 56 and ball bearings 58, 60. Shaft 54 is driven by stepper motor 62 via worm gear 64 and worm wheel 66. Mounted on shaft 54 is rotor disc member 84 of valve assembly 14. Also mounted on drive shaft 54 is encoder disc 70 that has radial edge surfaces defined by slots 72 and recess 74 that cooperate with optical sensors 76, 77, 78. Optical sensor 76 is mounted on guide rods 68 for lateral movement relative to encoder disc 70 as indicated in FIGS. 2 and 3. Adjusting screw 69 is threaded through support 71 of sensor 76 and biasing springs 73 bias support 71 to the right as viewed in FIG. 3 and urge the end of screw 69 against reference surface 75. Thus, the lateral position of sensor 76 may be varied to provide angular alignment of that sensor relative to encoder disc slots 72 and with ports in valve rotor 84. After sensor 76 has been appropriately aligned, set screw 77 locks sensor 76 to position on guide rods 68.

The valve assembly 14 includes stator disc members 80 and 82 and interposed rotor disc member 84, stator disc member 80 being biased against Delrin bearing spacer sleeve 83 by a biasing assembly on projecting extension 86 of shaft 54. Threadly secured to the end of and axially aligned with shaft 54 is shaft extension 86 on which is mounted compression spring 87 and collar 88 that has internal flange 89. Shaft extension 86 has knob 90 and shoulder 91. The biasing assembly as shown in FIG. 2 seats the valve members 80, 82, 84 in sealing relation with a force of about ten pounds that is maintained by spring 87 and allows easy disassembly of the valve for inspection, maintenance or otherwise as desired. On reassembly, shaft extention shoulder 91 is seated on the end of shaft 54 so that spring 87 reapplies the same biasing force on the valve assembly. Antirotation bar 94 prevents rotation of stators 80, 82.

Figure 4:
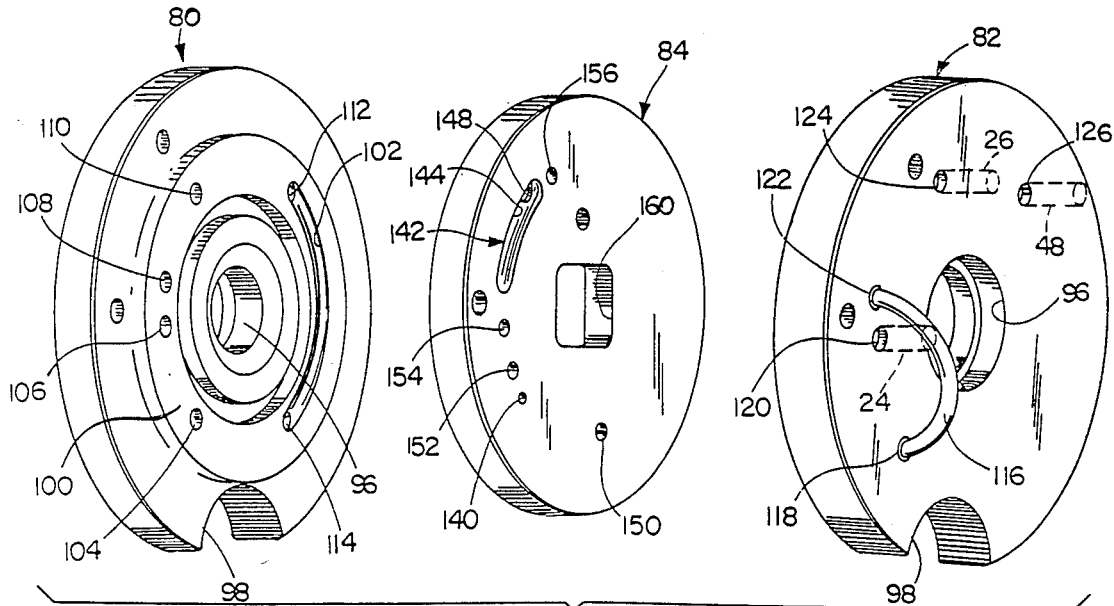
FIG. 4 is an exploded perspective view of components of the valve assembly shown in FIGS. 2 and 3.
Figure 5:
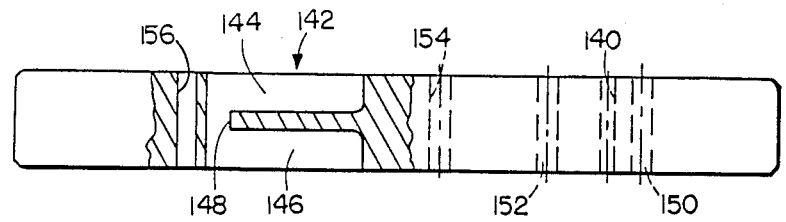
FIG. 5 is a side view (with parts broken away) of the rotor element shown in FIG. 4.

Further details of the valve discs 80, 82 and 84 may be seen with reference to FIGS. 4 and 5. These three valve members are of alumina ceramic with zero percent porosity and 12 GPa hardness (500 gram load Vickers). Stator members 80 and 82 each has a diameter of about 4.4 centimeters and a thickness of about 0.6 centimeters, a cylindrical bore 96 of about one centimeter diameter, and a recess 98 at its periphery that cooperates with antirotation bar 94. Each stator disc has a raised valving surface 100 of about three centimeters outer diameter. Formed in that surface at a radius of about 1.2 centimeters are a series of through passages and an arcuate groove 102 that has an angular length of about 100 degrees, a depth of about one millimeter, a width of about one millimeter and a smoothly curved base. Through passages 104, 106, 108, 110, 112 and 114 in stator disc 80 each have a diameter of about 0.8 millimeter; as do through passages 118, 120, 122, 124 and 126 in stator disc 82. Stainless steel coupling tube 116 (19 gauge and inner diameter of about 0.7 millimeter) is bonded in place with epoxy resin to through passages 118 and 122). Passage 104 is connected to sample line 12; passage 106 is connected to analyzer line 28; passage 108 is connected to waste line 42; passage 110 is connected to analyzer line 34; passage 112 is connected to cleaning fluid line 46; passage 114 is connected to waste line 43; through passage 120 connected to diluent line 24; through passage 124 connected to diluent inlet line 26; and through passage 126 connected to cleaning fluid inlet line 48.

Ceramic rotor disc 84 has a diameter of about 3.2 centimeter and a thickness of about 0.5 centimeter. Formed in rotor disc 84 at a radius of about 1.2 centimeter are 1.6 microliter metering through passage 140 of about 0.6 millimeter diameter; forty microliter arcuate metering chamber 142 that includes channels 144, 146 on opposed faces of rotor disc 84, (each with a width of about 1.2 millimeters and a depth of about 2 millimeters and a radiused bottom surface) that are in communication by through passage 148 of about 1.2 millimeter diameter (the same as the width of grooves 144, 146); and through passages 150, 152, 154 and 156, each of about one millimeter diameter. Square aperture 160 in rotor disc 84 receives drive shaft 54 in driving relation.

Coordinated with rotor disc 84 is the encoder disc 70 that has slots 72-1 (backlash), 72-2 (sample), 72-3 (dispense), and 72-4 (clean); and corroboration opening 74, each of which is defined by two radially extending surfaces that are sensed by sensors 76, 77 and 78 to signal the position of rotor disc 84.

Figure 6:
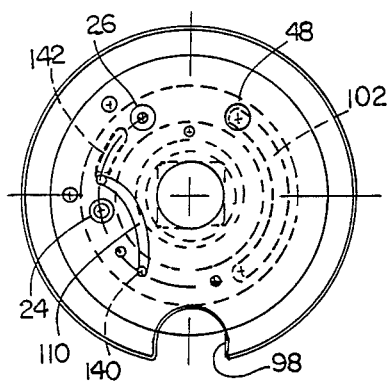
FIGS. 6, 7 and 8 are, respectively, an end view of the valve, a side view of the valve, and an end view that includes the encoder disc, in a first (sample) valve position.
Figure 7:
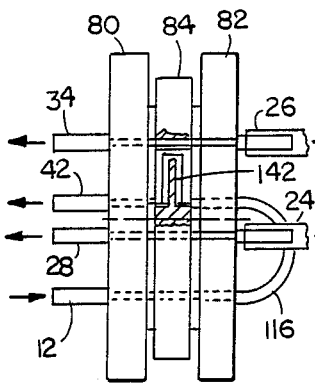
Figure 8:
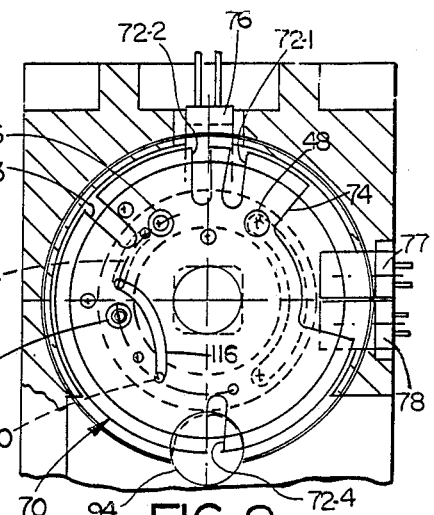
Figure 9:
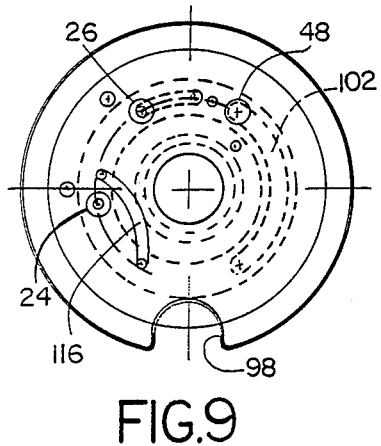
FIGS. 9–11 are views corresponding to those of FIGS. 6–8 of the valve and encoder disc in a second (dispense) position.
Figure 10:
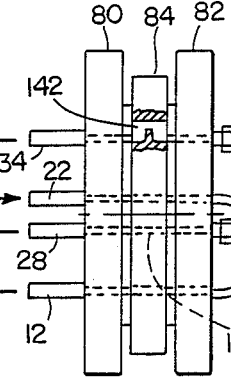
Figure 11:
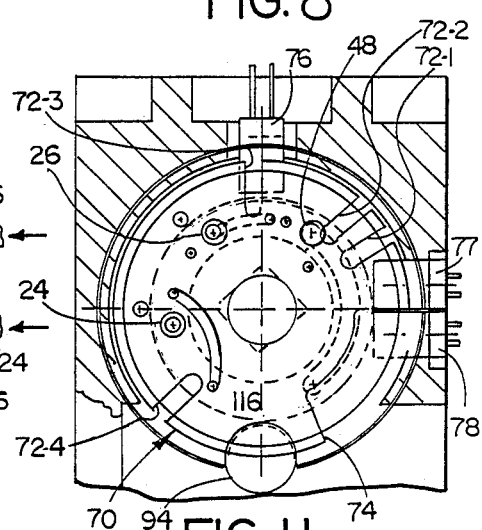
Figure 12:
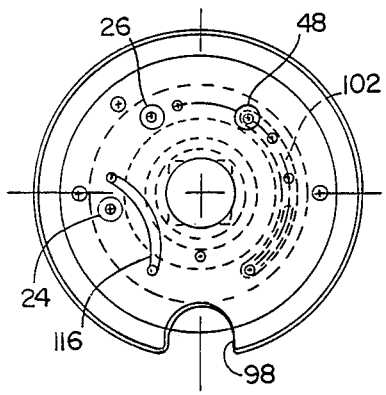
FIGS. 12–14 are views similar to FIGS. 6–8 and 9–11 of the valve and encoder disc in a third (cleaning) position of the valve.
Figure 13:
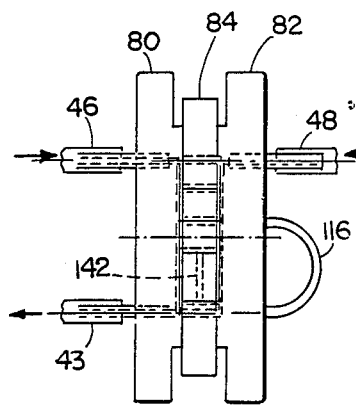
Figure 14:
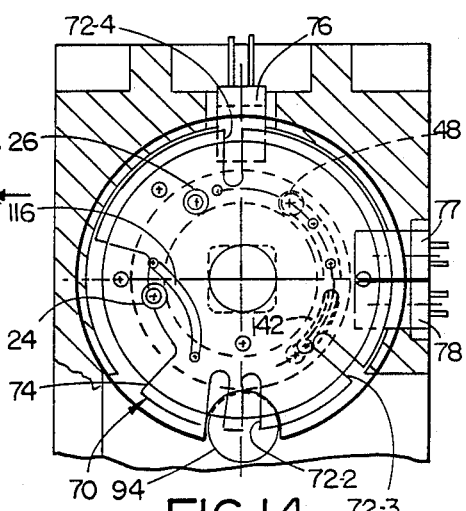

A sample position of the metering valve system is shown in FIGS. 6–8; a dispense position of the metering valve system is shown in FIGS. 9–11 and a cleaning position is shown in FIGS. 12–14. In the sample position (FIGS. 6-8) rotor 84 is positioned by stepping motor 62 to align the edge of encoder disc slot 72-2 with sensor 76 and neither corroboration sensor 77 or 78 is obstructed by encoder disc 70. In that position, metering passage 140 is aligned with stator passages 104 and 118 and with sample inlet 12. Loop 116 connects stator passage 118 to stator passage 122 which is aligned with the inlet end of groove 144 of arcuate metering chamber 142 and the outlet end of groove 146 is aligned with passage 108 in the stator disc 80 that is connected to waste line 42. Concurrently, diluent inlet 26 is in communication with analyzer line 34 through rotor passage 156 and diluent inlet 24 is in communication with analyzer line 28 through rotor passage 154. In this position, the blood sample to be analyzed is flowed from source 10 over line 12 and through metering passage 140, coupling loop 116 and metering chamber 142 to waste line 42. Thus, metering chambers 140 and 142 are filled with the blood sample to be analyzed. Concurrently, analyzer units 30 and 36 are flushed with diluent over lines 28 and 34.

Stepper motor 62 then rotates the rotor disc 84 47.7 degrees so that encoder slot 72-3 is sensed by sensor 76 and corroboration sensor 77 is obstructed by encoder disc 70 as indicated in FIG. 11. In this position, as indicated in FIGS. 9 and 10, arcuate metering channel 142 has its inlet end aligned with diluent line 26 and cylindrical metering passage 140 is aligned with diluent inlet line 24. Diluent from source 16 enters valve 14 through diluent inlet line 24 and flows the 1.6 microliter sample aliquot form metering chamber 140 over line 28 to RBC analyzer unit 30. Concurrently, diluent from source 16 enters valve 14 through diluent inlet line 26 and flows the forty microliter sample aliquot from metering chamber 142 over line 34 to WBC analyzer unit 36. In some cases, diluent from source 16 may also flow an aliquot of lyse through inlet line 24, metering chamber 142 and line 34 into WBC analyzer unit 36 behind the 40 microliter sample aliquot. Diluent is also flowed into line 22 for reverse flushing flow through rotor passage 152, coupling loop 116, rotor passage 150 and sample line 12.

In the RBC analyzer unit 30, an impedance measurement is made of total cells, cell volume and other values of the sample. In the WBC analyzer unit 36, after the blood sample is mixed with lysing reagent from source 38, an impedance measurement is made of the white blood cells that are intact after lysing, as well as an optical measurement of the cyano hemoglobin formed by reaction of the cyanide of the lysing reagent with the hemoglobin and lysed red cells.

In the valve cleaning position (FIGS. 12-14) stepper motor 62 rotates rotor shaft 54 to position sensor disc 70 with the edge of slot 72-4 sensed by sensor 76 and corroboration sensors 77, 78 are obstructed by disc 70. In this position, the arcuate cleaning channels 102 of the two stators are aligned with valve rotor chambers 140, 142 and passages 152, 154 and 156. In this position, cleaning fluid is flowed through lines 46, 48 into the arcuate cleaning channels 102 for flow through the rotor passages aligned with those channels and discharge through passage 114 and line 43 to waste container 35. After the rotor is soaked in the cleaning solution, the cleaning solution is rinsed from the pathways. If the system is to be returned to operation, diluent is used for the rinse; but if the system is to shut down, a rinse solution that contains preservatives but no salt is used. After the cleaning sequence is completed, stepper motor 62 returns the rotor 84 to backlash position (slot 72-1 with corroboration sensor 78 obstructed) and then to home position (slot 72-2 with neither sensor 77 or 78 obstructed) for receipt of a next sample to be analyzed.

While a particular embodiment of the invention has been shown and described, various modifications will be apparent to those skilled in the art, and therefore it is not intended that the invention be limited to the disclosed embodiment or to details thereof, and departures may be made therefrom within the spirit and scope of the invention.

What is claimed is:

1. A metering valve assembly for use in an analytical system comprising a fixed valve member and a movable valve member, said valve members having slidably engaged faces, one of said valve members including a first metering chamber in the form of a through passage having an axis perpendicular to the direction of relative valve member movement and a second metering chamber in the form of an elongated channel having a length at least three times its width and disposed along the direction of relative valve member movement, said metering chambers being connected in series for serial receipt of sample liquid to be analyzed in a first valve position, and said first metering chamber being connected in series between a source of auxiliary fluid and a first analysis unit and said second metering chamber being concurrently connected in series between a source of auxiliary fluid and a second analysis unit in a second valve position.

2. The metering valve assembly of claim 1 wherein said two metering chambers are in said movable valve member.

3. The metering valve assembly of claim 1 wherein said movable valve member has two parallel opposed faces and is interposed between two fixed valve members, and said opposed faces of said movable valve member are in slidable engagement with surfaces of said two fixed valve members.

4. The metering valve assembly of claim 1 wherein said second metering chamber has a volume at least ten times the volume of said first metering chamber.

5. The metering valve assembly of claim 1 wherein said movable valve member is a rotor member mounted for rotation between two stator members and said elongated metering chamber is of an arcuate configuration.

6. The metering valve assembly of claim 5 wherein said elongated arcuate metering chamber includes aligned inlet and outlet regions in opposite faces of said rotor member, two aligned grooves of arcuate configuration in opposed surfaces of said rotor member, a divider member between said arcuate grooves that extends from said inlet and outlet regions along the length of said arcuate grooves, and a through passage at the end of said arcuate chamber remote from said inlet and outlet regions.

7. The metering valve assembly of claim 1 wherein the volume of said first metering chamber is less than two microliters and the volume of said second metering chamber is greater than twenty microliters.

8. The metering valve assembly of claim 1 and further including a shaft on which said movable valve member is mounted, a stepper motor for driving said shaft, a plurality of sensors, and a position indicator disc mounted on said shaft, said indicator disc including an array of radially extending indicia that cooperate with said sensors to provide valve position information for controlling said stepper motor.

9. The metering valve assembly of claim 8 wherein said movable valve member is a rotor member mounted for rotation between two stator members and said second metering chamber is of an arcuate configuration and has a volume at least ten times the volume of said first metering chamber.

10. The metering valve assembly of claim 1 and further including a shaft on which said movable member is mounted, a reference member against which said fixed member is seated, a detachable external shaft extension, and biasing structure mounted on said shaft extension for urging said fixed and movable valve members into sealing engagement with one another.

11. The metering valve assembly of claim 10 wherein said movable valve member has two parallel opposed faces and is interposed between two fixed valve members, said opposed faces of said movable valve member are in slidable engagement with surfaces of said two fixed valve members, and said two metering chambers are in said movable valve member.

12. The metering valve assembly of claim 11 wherein said movable valve member is a rotor member mounted for rotation between two fixed valve members, and said second metering chamber is of an arcuate configuration and has a volume at least ten times the volume of said first metering chamber.

13. The metering valve assembly of claim 12 wherein said elongated arcuate metering chamber includes aligned inlet and outlet regions in opposite faces of said rotor member, two aligned grooves of arcuate configuration in opposed surfaces of said rotor member, a divider member between said arcuate grooves that extends from said inlet and outlet regions along the length of said arcuate grooves, and a through passage at the end of said arcuate chamber remote from said inlet and outlet regions.

14. The metering valve assembly of claim 13 wherein the volume of said first metering chamber is less than two microliters and the volume of said second metering chamber is greater than twenty microliters.

15. The metering valve assembly of claim 14 and further including a shaft on which said movable valve member is mounted, a stepper motor for driving said shaft, a plurality of sensors, and a position indicator disc mounted on said shaft, said indicator disc including an array of radially extending indicia that cooperate with said sensors to provide valve position information for controlling said stepper motor.

16. A metering valve assembly for use in an analytical system comprising
first and second valve members, said valve members having faces in slidable, sealing engagement with one another, one of said valve members including structure defining a first metering chamber in the form of a through passage having an axis perpendicular to the direction of relative valve member movement and structure defining a second metering chamber in the form of an elongated channel having a length at least three times its width and disposed along the direction of relative valve member movement,
said valve members having a first valve position in which said metering chambers are connected in series for serial receipt of sample liquid to be analyzed, and a second valve position in which said first metering chamber is connected in series between a source of auxiliary fluid and a first analysis unit and said second metering chamber is concurrently connected in series between a source of auxiliary fluid and a second analysis unit,
drive structure for producing relative movement of said first and second valve members between said first and second valve positions,
sensor structure disposed adjacent said drive structure, and
position indicator structure coupled to said drive structure adjacent said sensor structure, said indicator structure including a series of indicia that cooperate with said sensor structure to provide a first indication when said valve members are in said first valve position and a second indication when said valve members are in said second valve position.

17. The metering valve assembly of claim 16 wherein said drive structure includes a drive shaft, said position indicator structure includes an encoder disc, said indicia includes a series of radially disposed slots on said encoder disc, and said sensor structure is of the optical sensor type.

18. The metering valve assembly of claim 16 wherein said sensor structure includes a first sensor for sensing indicia on said position indicator structure and corroboration sensor structure for supplementing said first sensor.

19. The metering valve assembly of claim 16 wherein each of said valve members includes a plurality of flow passages, and further including means for varying the position of said sensor structure relative to said valve members to provide effective coordination of the position of said sensor structure with flow passages in one of said valve members.

20. The metering valve assembly of claim 16 wherein said drive structure includes a stepper motor and a drive shaft coupled between said stepper motor and a valve member, said position indicator structure includes an encoder disc fixedly mounted on said drive shaft, said indicia are openings in said encoder disc, and said sensor structure includes a first sensor for sensing said encoder disc openings, and a plurality of corroboration sensors cooperating with said encoder disc for providing supplementary identification of the encoder disc opening sensed by said first sensor.

21. The metering valve assembly of claim 16 wherein said one valve member is a rotor member mounted for rotation between two stator members, said second metering chamber is of arcuate configuration, the volume of said first metering chamber is less than two microliters, and the volume of said second metering chamber is greater than twenty microliters.

22. The metering valve assembly of claim 21 wherein said second metering chamber includes aligned inlet and outlet regions in opposite faces of said rotor member, two aligned grooves of arcuate configuration in opposed surfaces of said rotor member, a divider member between said arcuate grooves that extends from said inlet and outlet regions along the length of said arcuate grooves, and a through passage at the end of said arcuate chamber remote from said inlet and outlet regions.

23. The metering valve assembly of claim 21 and further including a shaft on which said rotor member is mounted, a stepper motor for driving said shaft, a plurality of sensors, and a position indicator disc mounted on said shaft, said indicator disc including an array of radially extending indicia that cooperate with said sensors to provide valve position indications.

* * * * *